US007635486B1

(12) United States Patent
Ades et al.

(10) Patent No.: US 7,635,486 B1

(45) Date of Patent: Dec. 22, 2009

(54) RECOMBINANT LIPIDATED PSAA PROTEIN, METHODS OF PREPARATION AND USE

(75) Inventors: Edwin W. Ades, Atlanta, GA (US); George M. Carlone, Stone Mountain, GA (US); Barun K. De, Snellville, GA (US); Jacquelyn S. Sampson, College Park, GA (US); Robert C. Huebner, Stroudsburg, PA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/600,057

(22) PCT Filed: Jan. 14, 1999

(86) PCT No.: PCT/US99/00379

§ 371 (c)(1), (2), (4) Date: Oct. 5, 2000

(87) PCT Pub. No.: WO99/40200

PCT Pub. Date: Aug. 12, 1999

(51) Int. Cl.
*A61K 39/02* (2006.01)
*A61K 45/00* (2006.01)
*A61K 39/09* (2006.01)

(52) U.S. Cl. ...................... 424/200.1; 424/9.1; 424/9.2; 424/184.1; 424/192.1; 424/234.1; 424/244.1; 424/278.1; 435/243; 435/252.1; 435/253.4

(58) Field of Classification Search .................. 424/9.1, 424/9.2, 184.1, 192.1, 200.1, 234.1, 244.1, 424/278.1; 435/243, 252.1, 253.4
See application file for complete search history.

(56) References Cited

FOREIGN PATENT DOCUMENTS

WO 93/10238 5/1993
WO 96/40718 12/1996

OTHER PUBLICATIONS

Ades et al., "Intranasal Immunization with Recombinant PsaA (37kDa) Protects Mice Challenged Intranasally with *Streptococcus pneumoniae," Centers for Diseases Control and Prevention, International Conference on Emerging Infectious Diseases* 1998 (Abstract).

Becker et al., "Recombinant Engineering of PspA Antigen from *Streptococcus pneumoniae* as a $PAM_3$cys-lipidated Protein Potentiates Immunogenicity for Both Parenteral and Mucosal Routes of Administration," *Vaccines* 97:39-44, 1997.

Bessler et al., "Synthetic lipopeptides as novel adjuvants," *Research in Immunology* 143(5):548-553, 1992.

Erdile et al., "OspA lipoprotein of *Borrelia burgdorferi* is a mucosal immunogen and adjuvant," *Vaccine* 15(9):988-995, 1997.

Sampson et al., "Cloning and Nucleotide Sequence Analysis of psaA, the *Streptococcus pneumoniae* Gene Encoding a 37-Kilodalton Protein Homologous to Previously Reported *Streptococcus* sp. Adhesins," *Infection and Immunity* 62(1):319-324, 1994.

Sampson et al., "Limited Diversity of *Streptococcus pneumoniae* psaA among Pneumococcal Vaccine Serotypes," *Infection and Immunity* 65(5):1967-1971, 1997.

Talkington et al., "Protection of mice against fatal pneumococcal challenge by immunization with pneumococcal surface adhesion A (PsaA)," *Microbial Pathogenesis* 21:17-22, 1996.

*Primary Examiner*—Rodney P. Swartz
(74) *Attorney, Agent, or Firm*—Klarquist Sparkman, LLP

(57) ABSTRACT

The present invention relates to recombinant lipidated PsaA proteins and recombinant constructs from which such lipidated PsaA proteins may be expressed. The invention relates further to lipidated PsaA proteins in which lipidation is effected by the use of a heterologous leader sequence derived from the ospA gene of *Borrelia burgdorferi,* which leader sequence is joined in translational reading frame with the psaA structural gene. The invention also provides methods of preparation of lipidated PsaA proteins and use of such proteins in immunological compositions. Also provided are vaccines comprising immunogenic lipidated PsaA proteins and methods of use of such vaccines in the prevention and treatment of *S. pneumoniae* infection.

14 Claims, No Drawings

RECOMBINANT LIPIDATED PSAA PROTEIN, METHODS OF PREPARATION AND USE

This is the U.S. National Stage of International Application No. PCT/US99/00379, filed Jan. 14, 1999, published in English under PCT Article 21(2), which claims the benefit of U.S. application No. 09/017,782, filed Feb. 3, 1998. Both applications are incorporated herein in their entirety.

BACKGROUND OF THE INVENTION

*Streptococcus pneumoniae* is an important cause of otitis media, meningitis, bacteremia and pneumonia, and a leading cause of fatal infections in the elderly and persons with underlying medical conditions, such as pulmonary disease, liver disease, alcoholism, sickle cell, cerebrospinal fluid leaks, acquired immune deficiency syndrome (AIDS), and patients undergoing immunosuppressive therapy. It is also a leading cause of morbidity in young children. Pneumococcal infections cause approximately 40,000 deaths in the U.S. each year (CDC. Prevention of Pneumococcal Disease. MMWR 1997; 46:1-25). The most severe pneumococcal infections involve invasive meningitis and bacteremia infections, of which there are 3,000 and 50,000 cases annually, respectively.

Despite the use of antibiotics and vaccines, the prevalence of pneumococcal infections has declined little over the last twenty-five years; the case-fatality rate for bacteremia is reported to be 15-20% in the general population, 30-40% in the elderly, and 36% in inner-city African Americans. Less severe forms of pneumococcal disease are pneumonia, of which there are 500,000 cases annually in the U.S., and otitis media in children, of which there are an estimated 7,000,000 cases annually in the U.S. caused by *S. pneumoniae.* Strains of drug-resistant *S. pneumoniae* are becoming ever more common in the U.S. and worldwide. In some areas, as many as 30% of pneumococcal isolates are resistant to penicillin. The increase in antimicrobial resistant pneumococcus further emphasizes the need for preventing pneumococcal infections.

Pneumococcus asymptomatically colonizes the upper respiratory tract of normal individuals; disease often results from the spread of organisms from the nasopharynx to other tissues during opportunistic events. The incidence of carriage in humans varies with age and circumstances. Carrier rates in children are typically higher than are those of adults. Studies have demonstrated that 38 to 60% of preschool children, 29 to 35% of grammar school children and 9 to 25% of junior high school children are carriers of pneumococcus. Among adults, the rate of carriage drops to 6% for those without children at home, and to 18 to 29% for those with children at home. It is not surprising that the higher rate of carriage in children than in adults parallels the incidence of pneumococcal disease in these populations.

An attractive goal for streptococcal vaccination is to reduce carriage in the vaccinated populations and subsequently reduce the incidence of pneumococcal disease. There is speculation that a reduction in pneumococcal carriage rates by vaccination could reduce the incidence of the disease in non-vaccinated individuals as well as vaccinated individuals. This “herd immunity” induced by vaccination against upper respiratory bacterial pathogens has been observed using the *Haemophilus influenzae* type b conjugate vaccines (Takala, A. K., et al., J. Infect. Dis. 1991; 164: 982-986; Takala, A. K, et al., Pediatr. Infect. Dis. J., 1993; 12: 593-599; Ward, J., et al., Vaccines, S. A. Plotkin and E. A. Mortimer, eds., 1994, pp. 337-386; Murphy, T. V., et al., J. Pediatr., 1993; 122; 517-523; and Mohle-Boetani, J. C., et al., Pediatr. Infect. Dis. J., 1993; 12: 589-593).

It is generally accepted that immunity to *Streptococcus pneumoniae* can be mediated by specific antibodies against the polysaccharide capsule of the pneumococcus. However, neonates and young children fail to make adequate immune response against most capsular polysaccharide antigens and can have repeated infections involving the same capsular serotype. One approach to immunizing infants against a number of encapsulated bacteria is to conjugate the capsular polysaccharide antigens to protein to make them immunogenic. This approach has been successful, for example, with *Haemophilus influenzae b* (see U.S. Pat. No. 4,496,538 to Gordon and U.S. Patent No. 4,673,574 to Anderson).

However, there are over ninety known capsular serotypes f *S. pneumoniae,* of which twenty-three account for about 85-90% of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all optimally immunogenic, even in adults.

Protection mediated by anti-capsular polysaccharide antibody responses is restricted to the polysaccharide type. Different polysaccharide types differentially facilitate virulence in humans and other species. Pneumococcal vaccines have been developed by combining the 23 different capsular polysaccharides which are representative of the prevalent types of human pneumococcal disease. These 23 polysaccharide types have been used in a licensed pneumococcal vaccine since 1983 (D. S. Fedson, M. Musher, Vaccines, S. A. Plotkin and J. E. A. Montimer, eds., 1994, pp. 517-564). The licensed 23-valent polysaccharide vaccine has a reported efficacy of approximately 60% in preventing bacteremia caused by vaccine type pneumococci in healthy adults.

However, the efficacy of the vaccine has been controversial, and at times, the justification for the recommended use of the vaccine questioned. It has been speculated that the efficacy of this vaccine is negatively affected by having to combine 23 different antigens. Having a large number of antigens combined in a single formulation may negatively affect the antibody responses to individual types within this mixture because of antigenic competition. The efficacy is also affected by the fact that the 23serotypes encompass all serological types associated with human infections and carriage.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

Russell et al. have described an immunogenic, species-common protein from *S. pneumoniae* designated pneumococcal fimbrial protein A. (J. Clin. Microbiol. 28: 2191-95 (1990)). This 37 kDa protein antigen is also described in U.S. Pat. No. 5,422,427, the teachings of which are hereby incorporated in their entirety herein by reference. The 37 kDa protein, which was previously referred to as pneumococcal fimbrial protein A, has more recently been designated pneumococcal surface protein A (PsaA). For the purposes of the present application, references made to PsaA, pneumococcal surface protein A, pneumococcal fimbrial protein A, or the 37 kDa antigen, shall all be understood to refer to that certain protein antigen from *S. pneumoniae* characterized by Russell et al. (1990) and described in U.S. Pat. No. 5,422,427.

Immunoblot analysis studies with a monoclonal antibody to PsaA demonstrate that PsaA is common to all 23 pneumococcal vaccine serotypes (Russell et al., 1990). The gene encoding PsaA has been cloned and sequenced. (Sampson et al. (1994) "Cloning and nucleotide sequence analysis of psaA, the *Streptococcus pneumoniae* gene encoding a 37-kilodalton protein homologous to previously reported Streptococcus sp. adhesins" Infect. Immun. 62:319-324. Unfortunately, the strain from which the gene was cloned, R36A, is an unencapsulated strain of low virulence, and subsequent studies have revealed that it is not representative of psaA genes from serotypes of clinically relevant strains. For example, oligonucleotide primers based on the published sequence of psaA from R36A were unable to direct PCR amplification of the psaA gene from strain D39, a virulent capsular type 2 strain (Berry and Paton. Infect. Immun. 64: 5255-62, 1996).

The psaA gene has been cloned from encapsulated strain 6B, and is the subject of patent application Ser. No. 08/222, 179, now abandoned. This gene is more representative of clinically relevant strains. This gene was initially cloned into pUC18 and subsequently inserted into an expression vector, pQE30 (Quiagen, Calif.) containing the T5 promoter. However, while *E. coli* host cells transformed with this construct and induced with IPTG did express recombinant PsaA, the recombinant cells were unstable and the yields were low. This instability may be due to the toxicity of naturally lipidated recombinant proteins to *E. coli* host cells, and makes such expression systems of limited use in preparation of sufficient quantities of recombinant. PsaA for use in immunological compositions.

In order to establish an infection, *S. pneumoniae* must first gain entry to the host through mucosal surfaces. The principal determinant of specific immunity at mucosal surfaces is secretory IgA (S-IgA) which is physiologically and functionally separate from the components of the circulatory immune system. Mucosal S-IgA responses are predominantly generated by the common mucosal immune system (CMIS) [Mestecky, J. Clin. Immunol. (1987), 7:265-276], in which immunogens are taken up by specialized lymphoepithelial structures collectively referred to as mucosa associated lymphoid tissue (MALT). The term common mucosal immune system refers to the fact that immunization at any mucosal site can elicit an immune response at all other mucosal sites. Thus, immunization in the gut can elicit mucosal immunity in the upper airways and vice versa.

Further, it is important to note that oral immunization can induce an antigen-specific IgG response in the systemic compartment in addition to mucosal IgA antibodies [McGhee, J. R. et al., (1993), Infect. Agents and Disease 2:55-73].

Most soluble and non-replicating antigens are poor mucosal immunogens, especially by the peroral route, probably because digestive enzymes degrade such antigens and such antigens have little or no tropism for the gut associated lymphoid tissue (GALT). Thus, a method for producing effective mucosal immunogens, and vaccines and immunogenic compositions containing them, would be desirable.

Native protein antigens such as PsaA, or immunogenic fragments thereof, stimulate an immune response when administered to a host. Recombinant proteins are promising vaccine or immunogenic composition candidates because they can be produced at high yield and purity and manipulated to maximize desirable activities and minimize undesirable ones. However, because they can be poorly immunogenic, methods to enhance the immune response to recombinant proteins are important in the development of vaccines or immunogenic compositions. Such antigens, especially when recombinantly produced, may elicit a stronger response when administered in conjunction with an adjuvant. An adjuvant is a substance that enhances the immunogenicity of an antigen. Adjuvants may act by retaining the antigen locally near the site of administration to produce a depot effect, facilitating a slow, sustained release of antigen to cells of the immune system. Adjuvants can also attract cells of the immune system, and may attract immune cells to an antigen depot and stimulate such cells to elicit an immune response.

Immunostimulating agents or adjuvants have been used for many years to improve the host immune response to, for example, vaccines. Intrinsic adjuvants, such as lipopolysaccharides, normally are components of the killed or attenuated bacteria used as vaccines. Extrinsic adjuvants are immunomodulators that are typically non-covalently linked to antigens and are formulated to enhance the host immune response. Aluminum hydroxide and aluminum phosphate (collectively commonly referred to as alum) are routinely used as adjuvants in human and veterinary vaccines. Currently, alum is the only adjuvant licensed for human use, although hundreds of experimental adjuvants such as cholera toxin B are being tested. However, these adjuvants have deficiencies. For instance, while cholera toxin B is not toxic in the sense of causing cholera, there is general unease about administering a toxin associated with a disease as harmful as cholera, especially if there is even the most remote chance of minor impurity. Also, it is generally believed that, for cholera toxin B to function effectively as an adjuvant, there must be some cholera toxin activity.

Thus, it would be desirable to enhance the immunogenicity of antigens, by methods other than the use of an adjuvant, especially in monovalent preparations; and, in multivalent preparations, to have the ability to employ such a means for enhanced immunogenicity with an adjuvant, so as to obtain an even greater immunological response.

A very promising immune stimulator is the lipid moiety N-palmitoyl-S-(2RS)-2,3-bis-(palmitoyloxy) propyl cysteine, abbreviated $Pam_3Cys$. This moiety is found at the amino terminus of the bacterial lipoproteins that are synthesized with a signal sequence that specifies lipid attachment and cleavage by signal peptidase II. Synthetic peptides that by themselves are not immunogenic induce a strong antibody response when covalently coupled to $Pam_3$ Cys [Bessler et al., Research Immunology (1992) 143:548-552].

In addition to an antibody response, one often needs to induce a cellular immune response, particularly cytotoxic T lymphocytes (CTLs). $Pam_3Cys$-coupled synthetic peptides are extremely potent inducers of CTLs, but no one has yet reported CTL induction by large recombinant lipoproteins.

As described in WO 90/04411, an analysis of the DNA sequence for the B31 strain of *B. burgdorferi* shows that the OspA protein is encoded by an open reading frame of 819 nucleotides starting at position 151 of the DNA sequence and terminating at position 970 of the DNA sequence (see FIG. 1 therein).

The first sixteen amino acid residues of OspA constitute a hydrophobic signal sequence of OspA. The primary translation product of the full length *B. burgdorferi* gene contains a hydrophobic N-terminal signal sequence which is a substrate for the attachment of a diacyl glycerol to the sulfhydryl side chain of the adjacent cysteine residue. Following this attachment, cleavag by signal peptidase II and the attachment of a third fatty acid to the N-terminus occurs. The complete lipid moiety is termed $Pam_3Cys$. It has been shown that lipidation of OspA is necessary for immunogenicity, since OspA lipoprotein with an N-terminal $Pam_3Cys$ moiety stimulates a strong antibody response, while OspA lacking the attached lipid does not induce any detectable antibodies [Erdile et al., Infect. Immun., (1993), 61:81-90].

Published international patent application WO 93/10238 describes the DNA sequence of the psaA gene of *S. pneumo-*

*niae* strain (type 6B) and the PsaA protein encoded thereby f 37 kDa molecular weight. This sequence reveals that PsaA is a lipoprotein that employs a signal sequence similar to that used for OspA. Based on the findings regarding OspA, one might expect that lipidation of recombinant PsaA would be useful to enhance its immunogenicity; but, as discussed below, the applicants experienced difficulties in obtaining detectable expression of recombinant PsaA.

U.S. Pat. No. 4,624,926 to Inouye relates to plasmid cloning vectors, including a DNA sequence coding for a desired polypeptide linked with one or more functional fragments derived from an outer membrane lipoprotein gene of a gram negative bacterium. The polypeptide expressed by the transformed *E. coli* host cells comprises the signal peptide of the lipoprotein, followed by the first eight amino acid residues of the lipoprotein, which in turn are followed by the amino acid sequence of the desired protein. The signal peptide may then be translocated naturally across the cytoplasmic membrane and the first eight amino acids of the lipoprotein may then be processed further and inserted into the outer membrane of the cell in a manner analogous to the normal insertion of the lipoprotein into the outer membrane. Immunogenicity of the expressed proteins was not demonstrated.

Published international patent application WO91/09952 describes plasmids for expressing lipidated proteins. Such plasmids involve a DNA sequence encoding a lipoprotein signal peptide linked to the codons for one of the β-turn tetrapeptides QANY or IEGR, which in turn is linked to the DNA sequence encoding the desired protein. Again, immunogenicity of the expressed proteins was not demonstrated.

SUMMARY OF THE INVENTION

It is an object of the invention to provide a recombinant pneumococcal lipoprotein wherein the lipidation thereof is from expression of a first nucleic acid sequence and the protein portion thereof is from expression of a second nucleic acid sequence and the first and second sequences do not naturally occur together; especially such a lipoprotein wherein the first sequence encodes a *Borrelia* lipoprotein leader sequence, preferably an OspA leader sequence, and more preferably wherein the second sequence encodes a protein portion comprising PsaA, or an immunogenic fragment thereof.

It is another object of the invention to provide expression of genes and/or sequences encoding such recombinant lipoproteins, vectors therefor and methods for effecting such expression.

It is a further object of the invention to provide immunogenic compositions, including vaccines, containing the recombinant lipoproteins and/or vectors for expression thereof.

Documents cited in this disclosure, including the above-referenced applications, provide typical additional ingredients for such compositions, such that undue experimentation is not required by the skilled artisan to formulate a composition from this disclosure. Such compositions should preferably contain a quantity of the recombinant PsaA lipoprotein or vector expressing such sufficient to elicit a suitable response. Such a quantity of recombinant lipoprotein or vector can be based upon known amounts of antigens administered. For instance, if there in a known amount for administration of an antigen corresponding to the second sequence expressed for the inventive recombinant lipoprotein, the quantity of recombinant PsaA lipoprotein can be scaled to about that known amount, and the amount of vector can be such as to produce a sufficient number of colony forming units (cfu) so as to result in in vivo expression of the recombinant lipoprotein in about that known amount. Likewise, the quantity of recombinant PsaA lipoprotein can be based upon amounts of antigen administered to animals in the examples below and in the documents cited herein, without undue experimentation.

The present invention also includes, in other aspects, procedures for the production of recombinant PsaA lipoproteins, by assembly of an expression vector, expression of the recombinant PsaA lipoprotein from a host organism containing the expression vector, and optionally isolating and/or purifying the expressed recombinant PsaA lipoprotein. The isolation and purification processes can be so as to obtain recombinant PsaA lipoprotein free from impurities such as lipopolysaccharides and other bacterial proteins. The present invention further includes immunogenic compositions, such as vaccines, containing the recombinant PsaA lipoprotein as well as methods for inducing an immunological response.

The present invention is concerned with genetic engineering to effect expression of pneumococcal lipoproteins from vectors containing nucleic acid molecules encoding the lipoproteins. More particularly, the present invention relates to expression of a recombinant PsaA lipoprotein wherein the lipidation thereof is from expression of a first nucleic acid sequence and the protein thereof is from expression of a second nucleic acid sequence, the first and second nucleic acid sequences, which do not naturally occur together, being contiguous. The invention relates to expression of such lipoproteins wherein the first nucleic acid sequence encodes a *Borrellia* lipoprotein (OspA) leader sequence. The invention also relates to recombinant lipidated PsaA proteins expressed using the nucleic acid sequence encoding the OspA leader sequence, methods of making and using the same compositions thereof and methods of using the compositions. The invention additionally relates to nucleic acid sequences encoding the recombinant PsaA lipoproteins, vectors containing and/or expressing the sequences, methods for expressing the PsaA lipoproteins and methods for making the nucleic acid sequences and vectors; compositions employing the PsaA lipoproteins, including immunogenic or vaccine compositions, such compositions preferably having improved immunogenicity; and methods of using such compositions to elicit an immunological or protective response.

Throughout this specification, reference is made to various documents so as to describe more fully the state of the art to which this invention pertains. These documents are each hereby incorporated herein by reference.

DETAILED DESCRIPTION OF THE INVENTION

The procedure of the present invention enables large quantities of pure recombinant, immunogenic lipidated PsaA proteins, and portions thereof, to be obtained, which has not heretofore been possible. The recombinantly-formed lipidated proteins provided herein are significantly more immunogenic than their non-lipidated recombinant analogs.

Accordingly, in one embodiment, the present invention provides an isolated hybrid nucleic acid molecule, preferably DNA, comprising a first nucleic acid sequence encoding the signal sequence preferably of an OspA protein of a *Borrelia* species, coupled in translational open reading frame relationship with a second nucleic acid sequence encoding a mature PsaA protein, or immunologically active fragment thereof.

The signal sequence of the OspA protein of a *Borrellia* strain encoded by the first nucleic acid sequence preferably is that of a strain of *B. burgdorferi,* more preferably a strain of *B.*

*burgdorferi* selected from the B31, ACAl and Ip90 families of strains, or from other strains with comparable signal sequences.

The hybrid gene provided herein may be assembled into an expression vector, preferably under the control of a suitable promoter for expression of the mature lipoprotein, in accordance with a further aspect of the invention, which, in a suitable host organism, such as *E. coli.* causes initial translation of a chimeric molecule comprising the leader sequence and the PsaA protein in lipidated form, followed by cleavage of the chimeric molecule by signal peptidase II and attachment of lipid moieties to the new terminus of the PsaA protein, whereby the mature lipoprotein is expressed in the host organism.

The present invention provides, for the first time, a hybrid nucleic acid molecule which permits the production of commercially useful quantities of recombinant lipidated PsaA protein, or immunologically active fragments thereof.

Recombinant methods are preferred since a high yield is desired. The basic steps in the recombinant production of lipidated PsaA include:

a) constructing a synthetic or semi-synthetic DNA encoding the heterologous PsaA lipoprotein, b) integrating said DNA into an expression vector in a manner suitable for the expression of the PsaA lipoprotein, either alone or as a fusion protein, c) transforming an appropriate prokaryotic or eukaryotic host cell with said expression vector, d) culturing said transformed or transfected host cell, and e) recovering and purifying the recombinantly produced PsaA lipoprotein.

For recombinant expression, the sequence coding for a PsaA lipoprotein may be wholly synthetic, semi-synthetic or the result of modification of the native psaA gene.

Synthetic genes, the in vitro or in vivo transcription and translation of which will result in the production of PsaA-like polypeptides may be constructed by techniques well known in the art. Owing to the natural degeneracy of the genetic code, the skilled artisan will recognize that a sizable yet definite number of DNA sequences may be constructed which encode PsaA lipoproteins. The gene encoding the PsaA lipoprotein may be created by synthetic methodology. Such methodology of synthetic gene construction is well known in the art. Brown, E. L., Belagaje, R., Ryan, M. J., and Khorana, H. G. (1979) in *Methods in Enzymology,* Academic Press, N.Y., Vol. 68, pgs. 109-151, the entire teaching of which is hereby incorporated by reference. The DNA segments corresponding to the psaA gene, or fragments thereof, are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404). The synthetic psaA gene may be designed to possess restriction endonuclease cleavage sites at either end of the transcript to facilitate isolation from and integration into expression and amplification plasmids. The choice of restriction sites are chosen so as to properly orient the sequence coding for the PsaA lipoprotein with control sequences to achieve proper in-frame reading and expression of the PsaA lipoprotein. A variety of other such cleavage sites may be incorporated depending on the particular recombinant constructs employed and may be generated by techniques well known in the art.

The "polymerase chain reaction" or "PCR" refers to a procedure or technique in which amounts of a pre-selected piece of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., Cold Spring Harbor Symp. Quant. Biol., 51, 263 (1987); Erlich, ed., PCR Technology, (Stockton Press, N.Y., 1989). PCR can also be used to conveniently introduce any desired sequence change genes of interest. See generally, Ausubel et al., eds, *Current Protocols in Molecular Biology,* § 8.5.1 (John Wiley & Sons, 1995).

Construction of suitable vectors containing the desired coding and control sequences employ standard ligation techniques. Isolated plasmids or DNA fragments are cleaved, tailored, and religated in the form desired to form the plasmids required.

To effect the translation of the desired PsaA lipoprotein sequence, one inserts the engineered DNA sequence coding for the PsaA lipoprotein in any of a plethora of appropriate recombinant DNA expression vectors through the use of appropriate restriction endonucleases. A synthetic version of the DNA coding sequence is designed to possess restriction endonuclease cleavage sites at either end of the transcript to facilitate isolation from and integration into these expression and amplification plasmids. The coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the DNA coding sequence with control sequences to achieve proper in-frame reading and expression of the PsaA lipoprotein.

In general, plasmid vectors containing promoters and control sequences that are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., Gene 2: 95 [1977]), pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

The DNA sequence coding for the PsaA lipoprotein must be positioned so as to be in proper reading frame with the promoter and ribosome binding site of the expression vector, both of which are functional in the host cell in which the DNA coding sequence for the PsaA lipoprotein is to be expressed. In the preferred practice of the invention, the promoter-operator region is placed in the same sequential orientation with respect to the ATG start codon of DNA sequence encoding the PsaA lipoprotein as the promoter-operator occupies with respect to the ATG-start codon of the gene from which it was derived. Synthetic or modified promoter-operator regions such as the tac promoter are well known in the art. When employing such synthetic or modified promoter-operator regions they should be oriented with respect to the ATG start codon of the DNA sequence coding for the PsaA lipoprotein as directed by their creators.

In general, prokaryotes are used for cloning of DNA sequences in constructing the vectors useful in the invention.

For example, *E. coli* K12 strain 294 (ATCC No. 31446) is particularly useful. Other microbial strains which may be used include *E. coli* B and *E. coli* X1776 (ATCC No. 31537), *E. coli* W3110 (prototrophic, ATCC No. 27325), bacilli such as *Bacillus subtilis,* and other enterobacteriaceae such as *Salmonella typhimurium* or *Serratia marcescans,* and various pseudomonas species may be used. Promoters suitable for use with prokaryotic hosts include the β-lactamase (vector pGX2907 [ATCC 39344] contains the replicon and β-lactamase gene) and lactose promoter systems (Chang et al., [1978] Nature, 275:615; and Goeddel et al., [1979] Nature 281:544), alkaline phosphatase, the tryptophan (trp) promoter system (vector pATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding PspA-like polypeptides using linkers or adapters to supply any required restriction sites. Promoters for use in bacterial systems also will contain a Shine-Dalgarno sequence operably linked to the DNA encoding the PspA-like polypeptide. These examples are illustrative rather than limiting.

While the discussion above and the examples provided herein refer to prokaryotic expression, those having skill in the art can readily appreciate that the recombinant PsaA lipoproteins of the instant invention may also be recombinantly produced in eukaryotic expression systems capable of effecting the necessary post translational lipid modifications.

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al. (1989) *Molecular Cloning: A Laboratory Manual,* Cold Spring Harbor Press, Cold Spring Harbor Laboratory, Cold Spring Harbor, N.Y. or *Current Protocols in Molecular Biology* (1989) and supplements.

The recombinant PsaA lipoproteins of the present invention may be made either by direct expression or as fusion protein comprising the PsaA lipoprotein followed by enzymatic or chemical cleavage. It is often observed in the production of certain peptides in recombinant systems that expression as a fusion protein prolongs the lifespan and/or increases the yield of the desired peptide. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., Carter P. Site Specific Proteolysis of Fusion Proteins, Ch. 13 in *Protein Purification: From Molecular Mechanisms to Large Scale Processes,* American Chemical Soc., Washington, D.C. (1990).

As described above, the hybrid gene can be assembled into an expression vector under the control of a suitable promoter for expression of the PsaA lipoprotein, which, in a suitable host organism, such a. *E. coli,* causes expression of the heterologous PsaA lipoprotein from the host organism.

The present invention also provides a recombinant PsaA lipoprotein expressed by a hybrid or chimeric gene comprising a first nucleic acid sequence encoding a leader or signal sequence contiguous with a second nucleic acid sequence encoding a protein portion of the PsaA lipoprotein, and the first and second sequences do not naturally occur together. The first and second sequences are preferably coupled in a translational open reading frame relationship.

The first and second sequences can be present in a gene; and the gene and/or the first and second sequences; can be in a suitable vector for expression. The vector can be a nucleic acid in the form of, e.g., plasmids, bacteriophages and integrated DNA, in bacteria, most preferably one used for expression, e.q. *E. coli, Bacillus subtilis, Salmonella, Staphylococcus, Streptococcus,* etc., or one used as a live vector, e.g. *Lactobacillus, Mycobacterium, Salmonella, Streptococcus,* etc. When an expression host is used the recombinant PsaA lipoprotein can be obtained by harvesting product expressed in vitro; e.g., by isolating the recombinant PsaA lipoprotein from a bacterial extract. The gene can preferably be under the control of and therefore operably linked to a suitable promoter and the promoter can either be endogenous to the vector, or be inserted into the vector with the gene.

The invention further provides vectors containing the nucleic acid encoding the recombinant PsaA lipoproteins and methods for obtaining the recombinant lipoproteins and methods for preparing the vectors.

As mentioned, the recombinant PsaA lipoproteins of the present invention can have enhanced immunogenicity. Thus, additional embodiments of the invention provide immunogenic or vaccine compositions for inducing an immunological response, comprising the isolated recombinant lipoprotein, or a suitable vector for in vivo expression thereof, or both, and a suitable carrier, as well as to methods for eliciting an immunological or protective response comprising administering to a host the isolated recombinant PsaA lipoprotein, the vector expressing the recombinant PsaA lipoprotein, or a composition containing the recombinant lipoprotein or vector, in an amount sufficient to elicit the response.

The present invention provides an immunogenic, immunological or vaccine composition containing recombinant polypeptides derived from pneumococcal strain(s), and a pharmaceutically acceptable carrier or diluent. An immunological composition containing the PsaA lipoprotein elicits an immunological response—local or systemic. The response can, but need not be, protective. An immunogenic composition containing the PsaA lipoprotein likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a host mammal comprising administering to the host an immunogenic, immunological or vaccine composition comprising a recombinant PsaA lipoprotein and a pharmaceutically acceptable carrier or diluent.

The determination of the amount of recombinant PsaA lipoprotein antigen and optional additional adjuvant in the inventive compositions and the preparation of those compositions can be in accordance with standard techniques well known to those skilled in the pharmaceutical or veterinary arts. In particular, the amount of antigen and adjuvant in the inventive compositions and the dosages administered are determined by techniques well known to those skilled in the medical or veterinary arts taking into consideration such factors as the particular antigen, the adjuvant (if present), the age, sex, weight, species and condition of the particular animal or patient, and the route of administration. For instance, dosages of particular PsaA lipoprotein antigens for suitable hosts in which an immunological response is desired, can be readily ascertained by those skilled in the art from this disclosure, as is the amount of any adjuvant typically administered therewith. Thus, the skilled artisan can readily determine the amount of antigen and optional adjuvant in compositions and to be administered in methods of the invention. Typically, an adjuvant is commonly used as 0.001 to 50 wt % solution in phosphate buffered saline, and the antigen is present on the order of micrograms to milligrams, such as about 0.0001 to about 5 wt %, preferably about 0.0001 to about 1 wt %, most preferably about 0.0001 to about 0.05 wt % (see, e.g., Examples below or in applications cited herein). Typically, however, the antigen is present in an amount on the order of micrograms to milligrams, or, about 0.001 to about 20 wt %, preferably about 0.01 to about 10 wt %, and most preferably about 0.05 to about 5 wt %.

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA analysis. Such determinations do not require undue experimentation from the knowledge of the skilled artisan, this disclosure and the documents cited herein. And, the time for sequential administrations can be ascertained without undue experimentation.

Examples of compositions of the invention include liquid preparations for orifice, e.g., oral, nasal, anal, vaginal, peroral, intragastric, mucosal (e.g., perlingual alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the PsaA lipoprotein antigen and optional additional adjuvant.

EXAMPLES

EXAMPLE 1

Derivation of PsaA Coding Sequence

Specifically designed oligonucleotide primers were used in a PCR procedure to amplify the psaA coding sequence from *S. pneumoniae* type 6B. Primers were based on the published psaA sequence. (Sampson et al., Infect. Immun. (1994) 62:319-324). Primer DE09 (SEQ ID NO: 1) covers 26 base pairs at the 5' end of the psaA gene. ending at the Sph1 site. Primer DE11 (SEQ ID NO: 2) encompasses 26 base pairs at the 3' end of the PsaA coding sequence and a BamH1 site.

```
                                        SEQ ID NO: 1
5' GGGCATGCGCTAGCGGAAAAAAAGAT

                                        SEQ ID NO: 2
3' GGGGATCCTTATTTTGCCAATCCTTC
```

Primer pairs DE09 and DE11 were used in a PCR reaction using the first strand DNA as a template to amplify an 870 base pair fragment. The PCR amplification was effected in a DNA Thermal Cycler (Perkin-Elmer Cetus) for 35 cycles, with denaturation for 30 seconds at 94° C., followed by an annealing reaction at 55° C. for 30 seconds with an extension at 72° C. for 2 minutes. The PCR-amplified psaA fragment was digested with Sph1 and BamH1 and ligated into the plasmid pLF100 (ATCC Accession No. 69750) which directs insertion downstream of, and in translational reading frame with, the ospA signal sequence and which had been digested with the same enzymes and purified by gel electrophoresis. The ligation of the PCR-amplified psaA fragment that had been digested with Sph1 and BamH1 into the pLF100 plasmid digested with the same enzymes resulted in the generation of plasmid pOPsaA.1.

The presence of the psaA gene of interest within this recombinant was confirmed by restriction fragment length polymorphism (RFLP) and cycle sequence analysis, using conventional techniques. The sequence of the recombinant lipidated PsaA is set forth in SEQ ID NO: 3. The first 52 residues are derived from the OspA signal sequence of *Borrelia burdorferi:* the remaining residues are derived from *S. pneumoniae* type 6B mature PsaA (lacking the native PsaA signal sequence).

Stable recombinant *E. coli* cells expressing recombinant rPsaA were prepared by transformation of competent HMS174-DE3 (Novagen Inc., Madison, Wisc.) cells with pOPsaA.1, using standard heat shock techniques (Novagen). Expression of recombinant PsaA was confirmed by immunoblot analysis with rabbit polyclonal anti-PsaA antibodies. One of several recombinants which expressed high levels of recombinant PsaA was designated HOPsaA.7.3 and subjected to further analysis. HopsAA was deposited with the American Type Culture Collection (ATCC) on Jan. 20, 1998 and given accession number 209590.

A single colony of recombinant HOPsaA.7.3 (DE3, $F^-$ recA, hsdR) was grown overnight (12-14 h) at 34° C. in 25 mL of Luria broth containing 0.8% NaCI and 100 ug/mL of carbenicillin. Next, 5 mL of the early log phase culture (~O.D.600: 0.7) was mixed with fresh 20 mL of the same broth and incubated with vigorous shaking at 34° C. for 2-3 h. Following induction with IPTG (0.4 mM) for 4-5 h the induced cells were pelleted by centrifugation @ 3000 rpm/25 min, resuspended in 2% Triton X114/ 67 mM PBS (7.5) and allowed to sit overnight. This process yielded two fractions: a detergent phase and an aqueous phase. Proteins from both phases were analyzed by 12% SDS-PAGE and visualized by silver staining. Western blot analysis was also performed with anti-PsaA antibodies to detect rPsaA in these phases. These experiments indicated that the detergent phase contained mostly two types of rPsaA with molecular masses 37 ka and 38 ka. It is not uncommon for recombinant lipidated proteins to appear as a doublet on SDS-PAGE gels. Slight variations in the degree of lipidation of these recombinant proteins may result in the subtle differences in apparent molecular weight observed on SDS-PAGE gels. These two proteins constituted >50% of total proteins present in the detergent phase as revealed by silver staining.

EXAMPLE 2

Purification of Recombination PsaA

To purify sufficient quantities of recombinant lipidated PsaA for use in vaccine studies, a stable recombinant HOPsaA.7.3 was used to prepare 1,000 mL of culture with the following modifications. Briefly, a single recombinant colony was grown overnight in 25 mL of Terrific broth™ (GIBCO BRL) containing 0.8% NaCI and 100 ug/mL of carbenicillin. The early log phase culture (25 mL) was added to 1000 mL of the same media, continued incubation for 8 h at 34° C. and was then induced with IPTG (0.4 mM) overnight (12-14 h). Cells were harvested and re-suspended in 100 mL of cold 2% Triton X-114/67 mM Phosphate buffer (pH7.6). Following sonication to effect lysis, the lysed cells were partitioned overnight at 4° C. Next, the lysate was clarified by centrifugation @ 10,000 rpm for 25 min at 4° C. and the clear supernatant was incubated at 37° C. for 20-25 min. to allow phase separation to occur. The detergent phase was separated from the aqueous phase by centrifugation @ 2500 rpm for 15 min at 25° C. and the viscous solution (10-12 ml) was washed with 100 mL of cold 67 mM PBS (pH 7.6) three times. The highly concentrated Triton™ X-114 phase (~8-10 mL), which contained the recombinant PsaA, was resuspended in 100 mL of cold 10 mM phosphate buffer (pH6.5) and dialyzed exhaustively against the same 10 mM phosphate buffer. Centrifugation of the dialysate @ 5000 rpm for 20 min at 4° C. yielded a clear solution and a visible pellet. The clear supernatant, greatly enriched for recombinant PsaA, was diluted up to ~200 mL with 10 mM phosphate buffer (pH6.5) and loaded directly to a D100 ion exchange filter pre-equilibrated with cold 10 mM phosphat (pH6.5) containing 0.1% Triton X-100 (flow rate 30-40 mL/h by gravity). Following extensive washes of the filter with a total of 250 mL of the same 10 mM phosphate buffer (pH 6.5)/0.1 % Triton X-100 (flow rate 50-60 mL/h), the filter was then eluted with 50 mL of buffer A (100 mM phosphate/0.1% Triton X-100, pH 6.5) followed by 50 mL of buffer B (100 mM phosphate/0.1% Triton X100/100 mM NaCI, pH 6.5). 10 ml fractions of the resultant eluates were analyzed by SDS-PAGE and visualized by silver nitrate staining. Western blot analysis was also performed with an anti-PsaA antibody to detect recombinant PsaA. The detergent phase contained two closely related recombinant PsaA proteins: (1) a major fraction which comigrated with the native protein of ~37 kDa eluted with the first three fractions of buffer A and (2) a slow migrating recombinant protein (~38 kDa) eluted with first two fractions of buffer B. These two recombinant PsaAs constituted >50% of total bacterial proteins which partitioned in the detergent phase as revealed by SDS-PAGE with silver nitrate staining. There were several minor contaminating *E. coli* proteins of low molecular weight also visualized in all fractions by silver nitrate staining but these were not detected by Western blot analysis. Using the Pierce BCA assay, total protein content of the detergent phase was estimated as 10 -12 mg/L of *E. coli* culture; the amount of purified recombinant PsaA eluted with buffer A is 700-750 ug/L using BSA as a standard (Note: approximate concentration of total detergent phase rPsaA is >2.5 mg/L of *E. coli* culture).

EXAMPLE 3

Immunogenicity of Recombinant Lipidated PsaA

A high-salt fraction of purified recombinant PsaA (DP2 ) was used as immunogen at two doses with alum. Swiss Webster mice were given 5 µg of DP2 at day 0 and boosted on day 14 with the same amount of rPsaA with alum. On day 21, animals were bled and the sera were tested for anti-PsaA antibodies by ELISA using purified native PsaA/rPsaA as the solid phase. All animals tested produced antibodies (≧1.5×$10^6$ titer) to PsaA.

In another experiment, High Five and Sf9 expressed recombinant PsaAs were used as immunogens at two dose levels with or without adjuvant (incomplete Freunds). Adult Swiss Webster mice were given either 20 ug or 5 ug of partially purified PsaAs at day 0 and boosted once on day 14 with the same amount of PsaAs without adjuvant. On day 21, animals were bled and the sera were tested for anti-PsaA antibody by dot blot assay using whole cells (serotype 6B), purified native and recombinant PsaAs, and also for titers to native PsaA.

All animals produced antibody that cross-reacted with the native and appropriate recombinant PsaAs with the exception of the antibody to Sf9 expressed PsaA, which showed limited cross-reactivity with the H5 expressed PsaA. Animals not receiving adjuvant had a reduced antibody titer (studies to determine most appropriate immunization schedule need to be done) in comparison to those receiving adjuvant.

A passive protection experiment using infant animals was performed. 20 ul of either control sera (no immunogen) or sera from immunized animals was given in 100 uL of PBS to infant mice 24 hours prior to challenge with serotype 6B (10×$BD_{100}$). Twenty-four hours post-challenge, 30% of animals were dead in the Sf9 protection group. Forty-eight hours post-challenge, 80% of the control sera group and 60% of the Sf9 group and 30% of the H5 group were dead. On day 10 post-challenge, 100% of the Sf9 group and the control group were dead whereas only 40% of the H5 group had died.

The ability of recombinant lipidated PsaA to confer active protection was also investigated. Adult and infant mice were immunized, with or without adjuvant (alum), using the recombinant PsaAs expressed by either Sf9 or H5. All infant mice given Sf9 expressed PsaA antigen (with or without alum) died within 24 hours post immunization (perhaps due to TritonX-114 toxicity) whereas all adults (immunized with Sf9 expressed PsaA) survived.

All animals were boosted on day 14 with immunogen only. On day 21, all animals were tested for antibody response by dot blot assay using the native and recombinant PsaAs and all appeared positive for antibody. On the same day, they were challenged with type 6B strain (700CFU). At 24 and 48 hours post-challenge all animals remained alive. 80% of control animals were bacteremic on day 2 whereas only 20% of infant animals (immunized with H5-rPsaA) were bacteremic. Adult data were inconclusive.

We claim:

1. Recombinantly produced, isolated and purified lipidated PsaA protein having a purity of at least 80%.

2. The recombinantly produced, lipidated PsaA protein of claim 1, wherein said protein has a purity of at least 95%.

3. An immunological composition comprising the recombinant lipidated PsaA protein of claim 1 and a pharmaceutically acceptable carrier or diluent.

4. The immunological composition of claim 3, further comprising an adjuvant.

5. The immunological composition of claim 4, wherein the adjuvant is alum.

6. A method of inducing an immunological response in an animal comprising the step of administering to the animal the immunological composition of claim 3.

7. A method of immunizing a host against pneumococcal infection, which method comprises administering to the host an immunologically effective amount of recombinantly produced, lipidated PsaA, wherein the lipidated PsaA is recombinantly produced in a High Five cell.

8. The method of claim 7, wherein said administration is effected intranasally.

9. An immunogenic composition for intranasal administration to a host susceptible to pneumococcal carriage to elicit a protective immunological response against colonization with *Streptococcus pneumoniae* in the nasopharynx, which comprises an immunizing amount of recombinant lipidated PsaA, or an immunogenic lipidated fragment thereof wherein the lipidated PsaA is recombinantly produced in a High Five cell.

10. The composition of claim 9, further comprising an adjuvant.

11. The composition of claim 10, wherein the adjuvant is alum.

12. A recombinant lipidated PsaA protein encoded by a hybrid nucleic acid molecule comprising a first nucleic acid sequence encoding a signal sequence of a lipoprotein other than PsaA and a second nucleic acid sequence, wherein the second nucleic acid sequence encodes a mature PsaA protein, and wherein the first nucleic acid sequence is contiguous with the second nucleic acid sequence.

13. The recombinant lipidated PsaA protein of claim 12, wherein the signal sequence is the signal sequence of an OspA protein of a *Borrelia* species.

14. The recombinant lipidated PsaA protein of claim 12, wherein the lipidated PsaA is produced in a High Five cell.

* * * * *

UNITED STATES PATENT AND TRADEMARK OFFICE

CERTIFICATE OF CORRECTION

PATENT NO. : 7,635,486 B1
APPLICATION NO. : 09/600057
DATED : December 22, 2009
INVENTOR(S) : Ades et al.

It is certified that error appears in the above-identified patent and that said Letters Patent is hereby corrected as shown below:

On the Cover:

(73) Assignee, "...and Human Services.", should be --...and Human Services, c/o Centers for Disease Control and Prevention.--.

After (87) and before (51), insert:

--Related U.S. Application Data

U.S. Application No. 09/017,782, filed on February 3, 1998--.

In the Specification:

Column 2, Line 13, "f" should be --of--.

Column 2, Line 43, "23serotypes" should be --23 serotypes--.

Column 4, Line 58, "cleavag" should be --cleavage--.

Column 5, Line 1, "f" should be --of--.

Column 11, Line 38, "perlingual alveolar" should be --perlingual, alveolar--.

Column 14, Line 24, "Recombination" should be --Recombinant--.

Column 14, Line 54, "phosphat" should be --phosphate--.

Signed and Sealed this

Nineteenth Day of October, 2010

David J. Kappos

*Director of the United States Patent and Trademark Office*

SEQUENCE LISTING

```
<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:Primer DE09
      covering 26 base pairs at the 5' end of the psaA
      gene, ending at the Sph1 site.

<400> SEQUENCE: 1

gggcatgcgc tagcggaaaa aaagat                                          26


<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:Primer DE11
      covers 26 base pairs at the 3' end of the PsaA
      coding sequence and a BamH1 site.

<400> SEQUENCE: 2

ggggatcctt attttgccaa tccttc                                          26
```

-continued

```
<210> SEQ ID NO 3
<211> LENGTH: 921
<212> TYPE: DNA
<213> ORGANISM: Artificial Sequence
<220> FEATURE:
<223> OTHER INFORMATION: Description of Artificial Sequence:Recombinant
      lipidated PsaA - first 52 residues drived from
      OspA signal sequence of B. burdorferi, remaining
      from S. pneumoniae type 6B PsaA.

<400> SEQUENCE: 3

atgaaaaaat atttattggg aataggtcta atattagcct taatagcatg cgctagcgga     60

aaaaaagata caacttctgg tcaaaaacta aaagttgttg ctacaaactc aatcatcgct    120

gatattacta aaaatattgc tggtgacaaa attgaccttc atagtatcgt tccgattggg    180

caagacccac acgaatacga accacttcct gaagacgtta agaaaacttc tgaggctgat    240

ttgattttct ataacggtat caaccttgaa acaggtggca atgcttggtt tacaaaattg    300

gtagaaaatg ccaagaaaac tgaaaacaaa gactacttcg cagtcagcga cggcgttgat    360

gttatctacc ttgaaggtca aaatgaaaaa ggaaaagaag acccacacgc ttggcttaac    420

cttgaaaacg gtattatttt tgctaaaaat atcgccaaac aattgagcgc caaagaccct    480

aacaataaag aattctatga aaaaaatctc aaagaatata ctgataagtt agacaaactt    540

gataaagaaa gtaaggataa atttaataag atccctgctg aaaagaaact cattgtaacc    600

agcgaaggag cattcaaata cttctctaaa gcctatggtg tcccaagtgc ctacatctgg    660

gaaatcaata ctgaagaaga aggaactcct gaacaaatca agaccttggt tgaaaaactt    720

cgccaaacaa aagttccatc actctttgta gaatcaagtg tggatgaccg tccaatgaaa    780

actgtttctc aagacacaaa catcccaatc tacgcacaaa tctttactga ctctatcgca    840

gaacaaggta aagaaggcga cagctactac agcatgatga aatacaacct tgacaagatt    900

gctgaaggat tggcaaaata a                                              921
```